United States Patent
Lou et al.

(10) Patent No.: US 9,192,339 B2
(45) Date of Patent: Nov. 24, 2015

(54) SCANNING SYSTEM AND IMAGE DISPLAY METHOD

(71) Applicant: Shenyang Neusoft Medical Systems Co., Ltd., Shenyang (CN)

(72) Inventors: Shanshan Lou, Shenyang (CN); Jian Zhao, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 95 days.

(21) Appl. No.: 14/142,953

(22) Filed: Dec. 30, 2013

(65) Prior Publication Data

US 2015/0104084 A1    Apr. 16, 2015

(30) Foreign Application Priority Data

Oct. 12, 2013   (CN) .......................... 2013 1 0477376

(51) Int. Cl.
   G06K 9/00      (2006.01)
   A61B 6/00      (2006.01)
(52) U.S. Cl.
   CPC ........................................ A61B 6/00 (2013.01)
(58) Field of Classification Search
   None
   See application file for complete search history.

(56) References Cited

U.S. PATENT DOCUMENTS

| | | | |
|---|---|---|---|
| 2003/0135119 A1* | 7/2003 | Lee ...................... | A61B 8/0833 600/461 |
| 2005/0054910 A1* | 3/2005 | Tremblay ............... | A61B 5/055 600/411 |
| 2007/0299352 A1* | 12/2007 | Harlev ................. | A61B 5/0422 600/509 |
| 2008/0045833 A1* | 2/2008 | Defreitas ............... | A61B 6/025 600/429 |
| 2010/0312096 A1* | 12/2010 | Guttman ................ | A61B 5/418 600/411 |

* cited by examiner

Primary Examiner — Jayesh A Patel
(74) Attorney, Agent, or Firm — Kilpatrick Townsend & Stockton LLP

(57) ABSTRACT

A scanning system and an image display method are provided, the method including: implementing a scanning process to obtain scanning data; converting the scanning data into image data; implementing an identification process and a segmentation process to the image data to obtain position and direction information of an interventional device; and calculating a first set of imaging parameters corresponding to a first image display mode based on the obtained position and direction information of the interventional device, and implementing real-time image display based on the first set of imaging parameters. Position and direction of interventional devices may be determined accurately. Further, multiple display modes are available, which may provide an accurate and full range image display.

6 Claims, 4 Drawing Sheets

SCANNING SYSTEM AND IMAGE DISPLAY METHOD

CROSS REFERENCE TO RELATED APPLICATIONS

The present application claims priority to Chinese Patent Application No. 201310477376.7, filed on Oct. 12, 2013 and entitled "SCANNING SYSTEM AND IMAGE DISPLAY METHOD", the entire disclosure of which is incorporated herein by reference.

FIELD OF THE DISCLOSURE

The present disclosure generally relates to image processing, and more particularly, to a scanning system and an image display method implemented on the scanning system.

BACKGROUND OF THE DISCLOSURE

Nowadays, scanning systems like computed tomography (CT) systems, magnetic resonance imaging (MRI) systems, and the like, are widely used in medical industry. Currently, scanning systems can be utilized in interventional therapy processes. For example, repeated scanning processes may be performed by using a CT system. Images obtained from the repeated scanning processes may be reconstructed and then be presented on a display device. Doctors can position an interventional device, such as a puncture needle, based on the CT image(s), so as to conduct an interventional therapy process.

In practical treatment processes, an interventional device, for example, a puncture needle, may have different directions depending on various positions and morphologies of different lesions. However, CT images are presented along an axial direction which may not be parallel with the puncture needle. As a result, the position and direction of the puncture needle can' be accurately controlled. Besides, in current techniques, projections of the puncture needle on other planes are not presented. Therefore, the relative position of the target lesion and the puncture needle may not be displayed clearly. Image display techniques with improved accuracy and a full range illustration are needed to facilitate medical treatments.

BRIEF SUMMARY OF THE DISCLOSURE

Embodiments of the present disclosure provided scanning systems and image display methods. Position and direction of interventional devices may be determined accurately. Further, multiple display modes are available, which may provide accurate and full range image display.

According to one embodiment of the present disclosure, an image display method is provided, the method may be used in a scanning system, the method may include:
implementing a scanning process to obtain scanning data;
converting the scanning data into image data;
implementing an identification process and a segmentation process to the image data to obtain position and direction information of an interventional device; and
calculating a first set of imaging parameters corresponding to a first image display mode based on the obtained position and direction information of the interventional device, and implementing real-time image display based on the first set of imaging parameters.

Optionally, the first image display mode includes at least one selected from multi-planar reformation display, curve-planar reformation display and three-dimensional display.

Optionally, when the first image display mode is multi-planar reformation display, the step of calculating a first set of imaging parameters corresponding to a first image display mode based on the obtained position and direction information of the interventional device, and implementing real-time image display based on the first set of imaging parameters includes:
determining imaging parameters for one or more imaging planes based on the obtained position and direction information of the interventional device, where the one or more imaging planes at least include a plane in which the interventional device is disposed, where the imaging parameters for anyone of the one or more imaging planes include coordinate information of a point on the corresponding plane, normal vector of the corresponding plane, size of the corresponding plane and information of local coordinate vectors of the corresponding plane;
establishing a three-dimensional image data set based on the image data obtained from the scanning process;
obtaining one or more multi-planar reformation images based on the three-dimensional image data set and the determined imaging parameters of the one or more imaging planes; and
displaying the multi-planar reformation images.

Optionally, the steps of obtaining one or more multi-planar reformation images based on the three-dimensional image data set and the determined imaging parameters of the one or more imaging planes and displaying the multi-planar reformation images include:
calculating coordinate information of a left-top point on anyone of the one or more imaging planes based on the coordinate information of the point on the corresponding plane, the normal vector of the corresponding plane, the size of the corresponding plane and the information of local coordinate vectors of the corresponding plane;
implementing traversal treatments to points on the one or more imaging planes, so as to obtain coordinate information of the points on the one or more imaging planes based on the coordinate information of the left-top points on the one or more imaging planes, respectively;
obtaining image pixel values corresponding to the coordinate information of the points on the one or more imaging planes based on the three-dimensional image data set and the obtained coordinate information of the points on the one or more imaging planes;
forming the one or more multi-planar images based on the obtained image pixel values; and
displaying the one or more multi-planar images.

Optionally, when the one or more imaging planes include more than one plane, the one or more imaging planes include at least a first imaging plane and a second imaging plane, where the first image plane is a plane in which the interventional device is disposed, and the second imaging plane is a plane perpendicular to the first imaging plane; or, the first image plane is a plane in which the interventional device is disposed, and the second imaging plane is any plane which is not parallel with the first imaging plane.

Optionally, when the first image display mode is curve-planar reformation display, the step of calculating a first set of imaging parameters corresponding to a first image display mode based on the obtained position and direction information of the interventional device, and implementing real-time image display based on the first set of imaging parameters includes:
determining imaging parameters of an imaging curve plane in which the interventional device is disposed based on the obtained position and direction information of the interventional device, where the imaging parameters include information of a curve line along which the interventional device is disposed and size of the curve plane;

establishing a three-dimensional image data set based on the image data obtained from the scanning process;

obtaining a curve-planar reformation image based on the three-dimensional image data set and the determined imaging parameters of the curve plane; and displaying the curve-planar reformation image.

Optionally, the method further includes:

after the position and direction information of the interventional device is obtained and before the imaging parameters of the imaging curve plane are determined based on the obtained position and direction information of the interventional device, determining whether the interventional device has a curve shape based on the obtained position and direction information of the interventional device, if yes, proceeding to the step of determining imaging parameters of an imaging curve plane in which the interventional device is disposed based on the obtained position and direction information of the interventional device.

Optionally, when the first image display mode is three-dimensional display, the step of calculating a first set of imaging parameters corresponding to a first image display mode based on the obtained position and direction information of the interventional device, and implementing real-time image display based on the first set of imaging parameters includes:

determining parameter information of an imaging camera plane based on the obtained position and direction information of the interventional device;

establishing a three-dimensional image data set based on the image data obtained from the scanning process;

obtaining a three-dimensional reformation image based on the three-dimensional image data set and the determined parameter information of the imaging camera plane; and displaying the three-dimensional reformation image.

Optionally, the steps of obtaining a three-dimensional reformation image based on the three-dimensional image data set and the determined parameter information of the imaging camera plane and displaying the three-dimensional reformation image includes:

implementing traversal treatments to points on the imaging camera plane, so as to cast a ray from each point on the imaging camera plane along a normal vector direction of the imaging camera plane;

calculating intersection points of the rays and the three-dimensional image data set;

taking the intersection points as sample points;

processing the sample points using image composition to form the three-dimensional reformation image; and displaying the three-dimensional reformation image.

According to one embodiment, a scanning system is provided, including:

a scanning device, adapted to implement a scanning process to obtain scanning data;

a reformation device, adapted to convert the scanning data into image data;

an identification device, adapted to implement an identification process and a segmentation process to the image data to obtain position and direction information of an interventional device; and a first image display device, adapted to calculate a first set of imaging parameters corresponding to a first image display mode based on the obtained position and direction information of the interventional device, and implement real-time image display based on the first set of imaging parameters.

Optionally, the scanning system is a computed tomography system or a magnetic resonance imaging system.

In an image display method of the present disclosure, a scanning process is implemented to obtain scanning data; the scanning data are converted into image data; an identification process and a segmentation process are implemented to the image data to obtain position and direction information of an interventional device; and a first set of imaging parameters corresponding to a first image display mode are calculated based on the obtained position and direction information of the interventional device, and real-time image display is implemented based on the first set of imaging parameters. The first image display mode may be any one of multi-planar reformation display, curve-planar reformation display and three-dimensional display. Position and direction of interventional devices may be determined accurately. Further, multi-planar reformation display, curve-planar reformation display and three-dimensional display are available based on the position and direction information, which may provide accurate and full range image display of relative positions of the interventional devices and lesions. Real-time, accurate and full range image display may be achieved.

BRIEF DESCRIPTION OF THE DRAWINGS

In order to clarify the disclosure and advantages thereof, accompanying drawings used in description of embodiments of the present disclosure will be described simply. Obviously, drawings described below are only illustrative and those skilled in the art can obtain other drawings based on these drawings without creative works.

DETAILED DESCRIPTION OF THE DISCLOSURE

Embodiments of the present disclosure provided scanning systems and image display methods. Position and direction of interventional devices may be determined accurately. Further, multiple display modes are available, which may provide an accurate and full range image display.

In order to clarify the objects, characteristics and advantages of the disclosure, embodiments of the disclosure will be interpreted in detail in combination with accompanied drawings. Apparently, embodiments disclosed hereinafter are merely examples, not all practical embodiments of the present disclosure. In light of the embodiments disclosed, other embodiments obtained by those skilled in the art without creative work should be included in the scope of the present disclosure.

Figure 1:
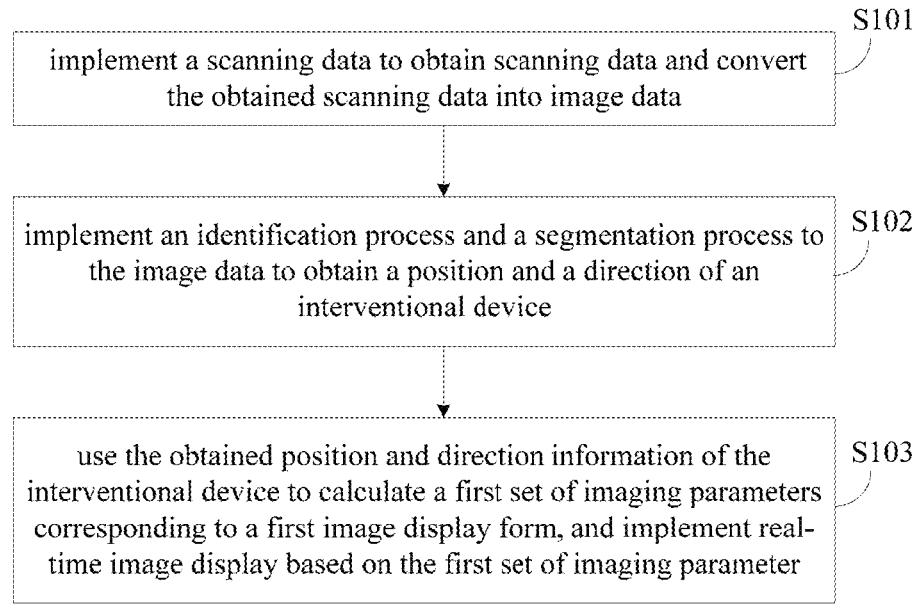
FIG. 1 schematically illustrates a flow chart of an image display method according to one embodiment of the present disclosure.

FIG. 1 schematically illustrates a flow chart of an image display method according to one embodiment of the present disclosure. The method may include steps S101, S102 and S103.

The method illustrated in FIG. 1 may be implemented by using a scanning system including but not limited to a CT system, a MRI system, or the like. In following descriptions, the scanning system may be a CT system and an interventional device used may be a puncture needle, which are merely an example for illustration. Those skilled in the art can understand that the scanning system may be a MRI system or the like, and the interventional device may be other device configured to be intervened into a human body.

In S101, implement a scanning data to obtain scanning data and convert the obtained scanning data into image data.

Figure 2:
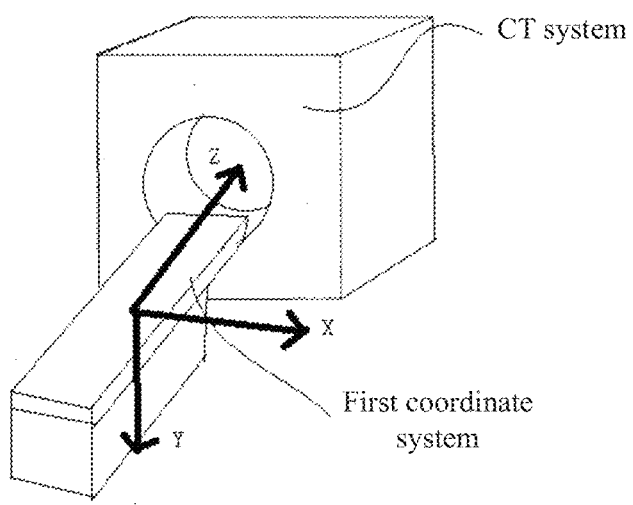
FIG. 2 schematically illustrates a human body in a first coordinate system according to one embodiment of the present disclosure.

In continues scanning processes, the CT system may obtain real-time scanning data and then convert the scanning data into image data. In some embodiments, multiple image display modes may be supported, which includes but not limited to multi-planar reformation (MPR) display, curve-planar reformation (CPR) display and 3D display. To realize the MPR, CPR or 3D display, a scanning range may be pre-determined, such that the scanning data can include 3D information. In such configuration, the MPR, CPR or 3D display may provide more practical clinical information. FIG. 2 schematically illustrates a human body in a first coordinate system. The first coordinate system may have a Z axis along an extension direction of the human body from head to feet. In some embodiments, the scanning range may be set as larger than or equal to about 20 mm on the Z axis, and the number of scanning frames may be set as greater than or equal to 10. Those skilled in the art can set the scanning range and other parameters according to practical requirements, which will not be illustrated in detail here.

It should be noted that, due to transmission speed limitation, conventional CT systems may not be capable of providing real-time display. In conventional techniques, a CT system may include a scanning device, a reformation computer and an image display computer. The scanning device implements scanning processes to obtain scanning data. Thereafter, the reformation computer implements image reformation computation to reform the scanning data into image data, and send the image data to the image display computer. The image display computer presents image(s) based on the image data. As the image data, which may normally include hundreds of megabytes, are transmitted from the reformation computer to the image display computer through LAN or direct cable connection, a relatively low transmission speed may be bottleneck of realizing real-time display.

In some embodiments, to realize real-time display, in a scanning system, a reformation computer and an image display computer may be integrated in a same device which may provide functions of both reformation computation and image display. Therefore, mass image data transmission through network may be overcome and real-time display may be achieved.

In some embodiments, the scanning system may still include a reformation device and an image display device respectively for reformation computation and image display. However, the reformation device/module may not only implement image reformation, i.e., converting scanning data into image data, but also process the image data to obtain images to be presented. The images to be presented, instead of the image data, are sent to the image display device. Compared with the reformed image data, the images to be presented may have a significantly reduced data size. Time for transmission may be greatly shortened and thus real-time display may be achieved. For example, the reformed image data may include data of about 100 reformed images, while the number of the image to be presented, set according to display parameters, may normally be 1 to 5. In such configuration, since only the images to be presented are transmitted, transmission efficiency may be increased. It should be noted that such configuration may increase computation load for the reformation device/module (for example, a computer). However, image reformation computation and image display computation are not parallel computations, which may not interfere with each other. Therefore, an ideal performance can be obtained.

In S102, implement an identification process and a segmentation process to the image data to obtain a position and a direction of an interventional device.

Specifically, after the image data are obtained, the interventional device in the reformed images may be identified and segmented to obtain the position and direction of the interventional device. Taking the interventional device being a puncture needle as an example, as the puncture needle may have a close-linear shape and outstandingly high CT values compared with human tissues around, it can be easily segmented by using a common image segmentation method. For example, the puncture needle may be segmented using a region grow method. Then a thinning algorithm may be implemented to obtain shape information (including two end points of the puncture needle), position information and direction information of the puncture needle. The direction of the puncture needle may be a direction along which the puncture needle enters into the human body. If the puncture needle is curved, a spline interpolation method may be used to obtain a fitted shape of the puncture needle. Specifically, points of the puncture needle may be identified using a region grow method and a thinning algorithm, then the points on the needle may be fitted using the spline interpolation method to obtain a spline, such as a Cardinal spline.

It should be noted that the position and direction information of the interventional device may include: position of a pin point of the interventional device, position of an end point of the interventional device (the end point may be a point from which the device intervenes into the human body, such as a intersecting point of the puncture needle and skin of the human body), position of a middle point of the interventional device, direction of the interventional device and length of the interventional device.

Taking the interventional device being a puncture needle as an example, the position and direction information may include:

(1) Pin point position: PinPoint (x, y, z);

(2) End point position: EndPoint (x, y, z), where the end point is an intersection of the puncture needle and skin of the human body;

(3) Middle point position: MidPoint (x, y, z), where the middle point is the middle of the puncture needle inside the human body, i.e., the middle between the pin point and the end point;

(4) Length: NeedleLength, representing length of the puncture needle inside the human body; and (5) Direction: NeedleDir (x, y, z), representing the direction of the puncture needle.

The direction of the puncture needle is a 3D vector calculated based on: NeedleDir=Pinpoint−EndPoint. Vector normalization may be implemented to the result of above calculation.

Specifically, suppose the vector NeedleDir have following components along three axial directions: NeedleDir.x, NeedleDir.y and NeedleDie.z, then the length of the vector is represented as follows.

NeedleLength=sqrt(NeedleDir.x*NeedleDir.x+
NeedleDir.y*NeedleDir.y+
NeedleDir.z*NeedleDir.z).

Therefore, the normalized vector components are represent as follows.

NeedleDir.x=NeedleDir.x/NeedleLength

NeedleDir.y=NeedleDir.y/NeedleLength

NeedleDir.z=NeedleDir.z/NeedleLength

As such, the position and direction of the puncture needle can be obtained.

In S103, use the obtained position and direction information of the interventional device to calculate a first set of imaging parameters corresponding to a first image display mode, and implement real-time image display based on the first set of imaging parameter.

The first image display mode may be a MPR form, a CPR form or a 3D display mode. Corresponding to different image display modes, the calculated imaging parameters may be different, which will be respectively illustrated hereinafter.

In some embodiments, the first image display mode is the MPR form. Therefore, using the obtained position and direction information of the interventional device to calculate the first set of imaging parameters corresponding to the first image display mode, and implementing the real-time image display based on the first set of imaging parameter may include: using the obtained position and direction information of the interventional device to determine imaging parameters of one or more planes, where the one or more imaging planes at least include a plane in which the interventional device is disposed, where the imaging parameters for each particular imaging plane of the one or more imaging planes may include coordinate information of a point in the particular imaging plane, normal vector of the particular imaging plane, size of the particular imaging plane and local coordinate vectors of the particular imaging plane; using the image data obtained from scanning to establish 3D image data set; obtaining one or more MPR images based on the 3D image data set and the determined imaging parameters of the one or more imaging planes; and displaying the one or more MPR images.

Specifically, obtaining the one or more MPR images based on the 3D image data and the determined imaging parameters of the one or more imaging planes, and displaying the one or more MPR images may include: calculating coordinate information of a left-top point of the particular imaging plane based on the coordinate information of the point in the particular imaging plane, the size of the particular imaging plane and the local coordinate vectors of the particular imaging plane; implementing a traversal treatment to each point in the particular imaging plane to obtain coordination information of each point in the particular imaging plane using the coordinate information of the left-top point of the particular imaging plane; obtaining pixel values corresponding to the coordinate information of each point in the particular imaging plane based on the 3D image data and the coordinate information of each point in the particular imaging plane; forming the one or more MPR images based on the pixel values; and displaying the one or more MPR images.

In some embodiments, the determined one or more imaging planes may include a first imaging plane and a second imaging plane, where the first imaging plane may be a plane in which the interventional device is disposed, and the second imaging plane may be a plane which is perpendicular to the first imaging plane or any plane not parallel with the first imaging plane.

Hereinafter, a specific example will be illustrated.

First, the first imaging plane in which the puncture needle is disposed may be calculated. Suppose the first imaging plane is RefPlane. To implement the multi-planar reformation, following information of the first imaging plane RefPlane may be calculated:

(1) Position of a point in the first imaging plane: RefPlanePos (x, y, z), where x, y and z represent coordinator values of the point;

(2) Normal vector of the first imaging plane: RefPlaneNormal (x, y, z);

(3) Size of the first imaging plane: the size may be defined as a width of the first imaging plane RefPlaneWidth and a height of the first imaging plane RefPlaneHeight, which can be used to represent the size of the first imaging plane; and (4) Local coordinate vectors of the first imaging plane: the local coordinate vectors may be two orthogonal 3D vectors disposed in the first imaging plane, which are a plane row vector RefPlaneRowVec (x, y, z) and a plane column vector RefPlaneColVec (x, y, z) to be mapped as the row vector (from left to right) and the column vector (from top to bottom) in a MPR image.

How to calculate the imaging parameters of the first imaging plane will be illustrated hereinafter.

Since the puncture needle is disposed in the first imaging plane, the middle point of the puncture needle may be set as the point in the first imaging plane. Thus, we obtain:

RefPlanePos(x,y,z)=MidPoint(x,y,z).

To determine the normal vector of the first imaging plane, it is only necessary to ensure that the normal vector is perpendicular to the direction of the puncture needle NeedleDir. Specifically, the normal vector may be calculated by: determining a second vector which is not parallel with the needle direction NeedleDir; and determining a vector perpendicular to both the NeedleDir and the second vector as the normal vector of the first imaging plane.

Figure 3:
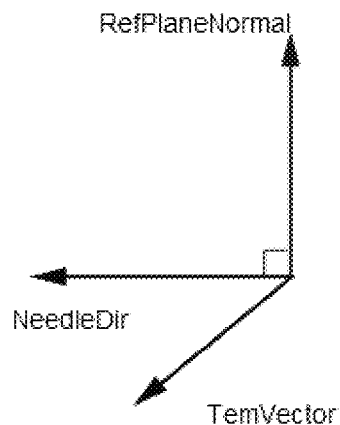
FIG. 3 schematically illustrates a normal direction of a first imaging plane according to one embodiment of the present disclosure.

FIG. 3 schematically illustrates a normal direction of the first imaging plane according to one embodiment. Referring to FIG. 3, a 3D vector TemVector which is not parallel with the needle direction NeedleDir is determined. Since the NeedleDir is absolutely not parallel with at least one vector of V1 (1, 0, 0), V2 (0, 1, 0) and V3 (0, 0, 1), the TemVector may be calculated as follows. Dot products of the needle direction NeedleDir and any one of the vectors V1, V2 and V3 are calculated. If any dot product is less than 1, it could be determined that the vector corresponding to the dot product is not parallel with the vector NeedleDir. For example, the dot product of the needle direction and the vector V1, DotProduct (NeedleDir, V1), is less than 1, then the vector V1 can be determined not parallel with the needle direction and we obtain: TemVector=V1.

DotProduct represents a dot product of two vectors. For example, the dot product of a vector Va (x, y, z) and a vector Vb (x, y, z) can be calculated as follows.

DotProduct(Va,Vb)=Va.x*Vb.x+Va.y*Vb.y+Va.z*Vb.z

Thereafter, the normal vector of the first imaging plane may be calculated using the determined second vector TemVector as follows.

RefPlaneNormal(x,y,z)=CrossProduct(TemVector,
NeedleDir)

CrossProduct represents a cross product calculation of two 3D vectors U (u1, u2, u3) and V (v1, v2, v3). If the two vectors U and V are not parallel, their cross product shall be a vector S (s1, s2, s3) perpendicular to both of them. Calculation of components of the vector S may be implemented as follows.

$$s1 = u2*v3 - u3*v2$$

$$s2 = u3*v1 - u1*v3$$

$$s3 = u1*v2 - u2*v1$$

As such, the normal vector of the first imaging plane can be determined. Thereafter, the size of the first imaging plane may be set as the same as the size of scanned images. for example, the width and height of the scanned images are set as 512*512, then we obtain: RefPlaneWidth=512, and RefPlaneHeight=512.

How to calculate the local coordinate vectors RefPlaneRowVec (x, y, z) and RefPlaneColVec (x, y, z) will be illustrated hereinafter. Since the puncture needle is disposed in the first imaging plane, and so is disposed in an image corresponding to the first imaging plane, the two local coordinate vectors may be set as follows.

RefPlaneColVec=NeedleDir

RefPlaneRowVec=CrossProduct (RefPlaneNormal,NeedleDir)

As such, the column vector of the first imaging plane is set to be the same as the direction of the puncture needle, and the row vector of the first imaging plane is set based on the cross product of the normal vector of the first imaging plane and the needle direction.

Based on above processing, parameters required to establish the first imaging plane may be determined. Thereafter, multi-planar reformation may be performed based on the imaging parameters of the first imaging plane. Specifically, 3D image data may be established using the image data obtained from the scanning, then a MPR image may be obtained based on the established 3D image data and the determined imaging parameters of the first imaging plane. The image data obtained from the scanning processes implemented by the CT system may be 2D tomography images (i.e., the scanned images). The 3D image data set VolumeData may be established by composing these 2D tomography images along the scanning direction (i.e., Z axis direction illustrated in FIG. 2). The 3D image data set VolumeData may include image data of points in a cuboid, in which each point may be represented as Volume [x, y, z].

In practice, interpolation of the first imaging plane in the 3D image data set VolumeData may be implemented to realize the multi-planar reformation. Intersection points (InterpolatePnt [x, y, z]) of the first imaging plane and the cuboid of the 3D image data set VolumeData may be calculated, which points constituting the MPR image: Image.

Specifically, coordinate information of the left-top point RefPlaneCorner in the first imaging plane may be calculated as follows.

RefPlaneCorner=RefPlanePos−
(RefPlaneColVec*RefPlaneHeight/2+
RefPlaneRowVec*RefPlaneWidth/2)

Thereafter, a traversal treatment may be performed to each point in the first imaging plane to obtain coordinate information PlanePnt of each point in the first imaging plane using the coordinate information of the left-top point. PlanePnt may be calculated as follows:

PlanePnt=RefPlaneCorner+(RefPlaneColVec*j+
RefPlaneRowVec*i)

where i and j are integer numbers ranging from 0 to 511.

Thereafter, pixel value pixelValue of the point in the 3D image data set VolumeData may be calculated as follows.

pixelValue=VolumeData[PlanePnt.x,PlanePnt.y,
PlanePnt.z]

Therefore, the pixel value of the point in the MPR image may be obtained as follows.

Image [i,j]=pixelValue

As such, the MPR plane may be obtained

In some embodiments, the determined one or more imaging planes may include a first imaging plane and a second imaging plane, where the first imaging plane may be a plane in which the interventional device is disposed, and the second imaging plane may be a plane which is perpendicular to the first imaging plane or any plane not parallel with the first imaging plane.

Figure 4:
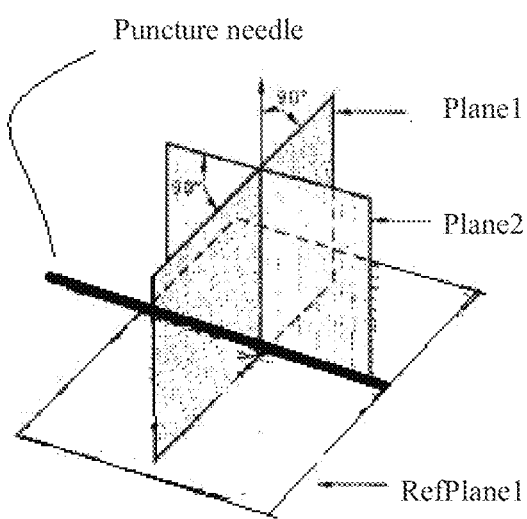
FIG. 4 schematically illustrates multiple planes according to one embodiment of the present disclosure.

In some embodiments, the system may automatically calculate to obtain a plane Plane1 and a plane Plane2 perpendicular to the first imaging plane RefPlane (as shown in FIG. 4). Both the Plane1 and the Plane2 pass through the point RefPlanePos in the first imaging plane. The normal vector of the Plane1 is the direction of the puncture needle NeedleDir. The puncture needle is disposed in the Plane2, so the Plane2 is parallel with NeedleDir. Therefore, the normal vector Plane2Normal of the Plane2 is perpendicular to NeedleDir and RefPlaneNormal. Plane1 and Plane2 have the same size as RefPlane.

Specifically, parameters of Plane1 may be set as follows:

(1) Position of a point in Plane1: set as the same point selected in the first imaging plane, i.e., Plane1Pos=RefPlanePos;

(2) Normal vector of Plane1: set as the direction of the puncture needle, i.e., Plane1Normal=NeedleDir, (3) Size of Plane1: set as the same as the first imaging plane, i.e., Plane1 Width=RefPlaneWidth, and Plane1Height=RefPlaneHeight; and (4) Local coordinate vectors of Plane1: the row vector of Plane1 is set as the row vector of the first imaging plane, and the column vector of Plane1 is set as the normal vector of the first imaging plane, i.e., Plane1RowVec=RefPlaneRowVec, and Plane1ColVec=−RefPlaneNormal.

For Plane2, its parameters may be set as follows:

(1) Position of a point in Plane2: set as the same point selected in the first imaging plane, i.e., Plane2Pos=RefPlanePos;

(2) Normal vector of Plane2: set as the cross product of the normal vector of the first imaging plane and the direction of the puncture needle, i.e., Plane1Norma2=CrossProduct (NeedleDir,RefPlaneNormal);

(3) Size of Plane2: set as the same as the first imaging plane, i.e., Plane2Width=RefPlaneWidth, and Plane2Height=RefPlaneHeight; and (4) Local coordinate vectors of Plane2: the row vector of Plane1 is set as the inverse direction of the needle direction, and the column vector of Plane1 is set as the inverse of the normal vector of the first imaging plane, i.e., Plane2 RowVec=−NeedleDir, and Plane2ColVec=−RefPlaneNormal.

It should be noted that, the symbol "−" represents an inversed direction.

Figure 5:
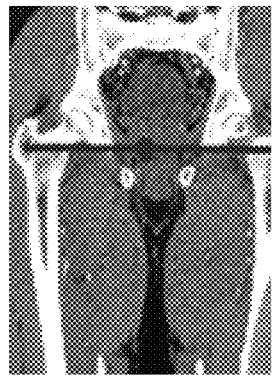
FIG. 5 schematically illustrates in interface for defining a plane according to one embodiment of the present disclosure.

In some embodiments, other imaging planes may be any planes which are not parallel with the first imaging plane, as long as the interventional device is disposed in the first imaging plane. Specifically, to meet different requirements of different users, plane positioning and varying application may be installed in an image display module of the scanning system. A positioning line (as shown in FIG. 5) may be provided in MPR. The positioning line may be an intersection line between another MPR plane and the first imaging plane. To define a new plane, a user can move or rotate the positioning line. Accordingly, the system may calculate a new plane based on position and angle of the moved or rotated positioning line, and the image display module may implement multi-planar reformation based on the new plane.

Above described embodiments regarding MPR form, which are merely examples and shall not limit the scope of the present disclosure.

In some embodiments, curve-planar reformation form may be used as the first image display mode. Therefore, using the obtained position and direction information of the interventional device to calculate the first set of imaging parameters corresponding to the first image display mode, and implementing the real-time image display based on the first set of imaging parameter may include: using the obtained position and direction information of the interventional device to determine imaging parameters of an imaging curve plane in which the interventional device is disposed, where the imaging parameters may include curve line information of the interventional device and size of the curve plane; using the image data obtained from scanning to establish 3D image data; obtaining a CPR image based on the 3D image data and the determined imaging parameters of the imaging curve plane; and displaying the CPR image.

In some embodiments, after the position and direction information of the interventional device are obtained, and before the imaging parameters of the imaging curve plane in which the interventional device is disposed are obtained using the obtained position and direction information of the interventional device, the method may further include: determining whether the interventional device has a curve shape based on the obtained position and direction information of the interventional device, if yes, implementing the step of using the obtained position and direction information of the interventional device to determine imaging parameters of an imaging curve plane in which the interventional device is disposed.

Taking the interventional device is a puncture needle as an example, how to determine whether it has a curve shape will be illustrated as follows.

If the puncture needle has a curve shape, to implement the CPR display, a curve line may be calculated to simulate the shape of the puncture needle. A curve image may be presented using CPR based on the curve line, so as to assist observing issues along the puncture needle.

To determine whether or not a CPR is needed, whether or not the puncture needle is curve may be determined according to whether or not two straight lines respectively passing through the pin point and the end point of the puncture needle are parallel. Specifically, suppose PinPoint (x, y, z) stands for the pin point of the puncture needle, EndPoint (x, y, z) stands for the end point of the puncture needle, and MidPoint (x, y, z) stands for the middle point of the puncture needle.

A vector V1 from Midpoint to PinPoint may be set as: V1=PinPoint−MidPoint.

A vector V2 from EndPoint to MidPoint may be set as: V2=MidPoint−EndPoint.

After vector normalization, if the two normalized vectors V1 and V2 are not parallel, i.e., DotProduct (V1, V2)<1, the puncture needle may be determined to be curve. Thus, CPR may be implemented. A curve plane CPRPlane need to be determined, which require following parameters:

(1) 3D curve line parameters Curve: the 3D curve line is a simulation of the needle shape, which is constituted by a plurality of 3D points disposed on the puncture needle;

(2) Size of the curve plane CurvePlaneLength: the size indicates a width of an image formed by CPR, the width of the image is a distance along a direction perpendicular to the 3D curve line; and (3) Extension direction of the curve plane CurvePlaneDir: the curve plane is establish by extending the curve line along the extension direction CurvePlaneDir.

How to implement the CPR process will be illustrated as follows.

1. Calculate the curve line parameters Curve, the size of the curve plane CurvePlaneLength and the extension direction of the curve plane CurvePlaneDir.

Figure 6:
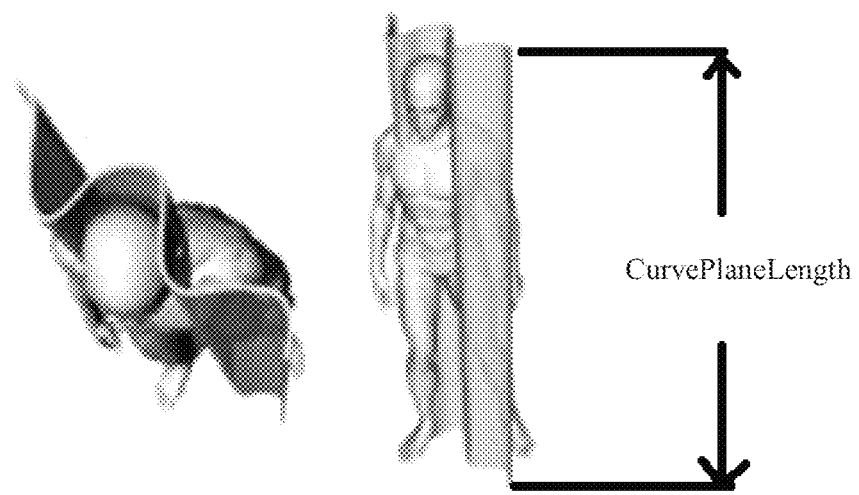
FIG. 6 schematically illustrates a curve plane according to one embodiment of the present disclosure.

Suppose the puncture needle have following sample points: CurveP1, CurveP2, ... CurvePn, where n stands for the number of the sample points. Connect these sample points, and such that the curve line Curve can be obtained. The size of the curve plane CurvePlaneLength may be set to be the same as the width of scanned images, reference of which can be obtained in FIG. 6.

The extension direction of the curve plane CurvePlaneDir can be calculated as follows.

When whether the puncture needle has a curve shape is determined in above processing, two vectors V1 and V2 are obtained. The extension direction CurvePlaneDir may be set as a vector perpendicular to the plane where the puncture needle is disposed, i.e., perpendicular to both the two vector V1 and V2. Therefore, the extension direction of the curve plane may be calculated as follows.

CurvePlaneDir=CrossProduct(V1,V2)

2. Display the curve plane using a CPR method.

CPR imaging is similar to MPR imaging. The above two processes differ in that the imaging plane in the CPR process is corresponding to a curve plane, not a flat plane as in the MPR process. To calculate pixel value of each point on the CPR image, a traversal treatment may be performed to each point in the curve plane to obtain its corresponding 3D coordinate values in the 3D image data set VolumeData. Values of points with corresponding coordinates in VolumeData are pixel values of points in the CPR image.

In some embodiments, the first image display mode may be a 3D display mode. When the first image display mode is 3D display mode, the step of using the obtained position and direction information of the interventional device to calculate the first set of imaging parameters corresponding to the first image display mode, and implementing the real-time image display based on the first set of imaging parameter may include: using the obtained position and direction information of the interventional device to determine imaging parameters of an imaging camera plane; using the image data obtained from scanning to establish 3D image data; obtaining a 3D reformation image based on the 3D image data and the determined imaging parameters of the imaging camera plane; and displaying the 3D reformation image.

Specifically, the step of obtaining a 3D reformation image based on the 3D image data and the determined imaging parameters of the imaging camera plane; and displaying the 3D reformation image may include: implementing a traversal treatment to each point on the imaging camera plane, where a ray is casted from each point on the imaging camera plane along a normal vector direction of the imaging camera plane: calculating intersection points of the casted rays and the 3D image data to obtain sample points; processing the sample points to form a 3D reformation image; and displaying the 3D reformation image.

Detail descriptions of the 3D image display will be illustrated hereinafter. Volume rendering may be used to implement the 3D image display.

Following parameters may be calculated for volume rendering:

(1) 3D image data set VolumeData: the 3D image data may be obtained by composing along the Z axis 2D images obtained from scanning processes; and (2) Imaging camera plane parameter information CamerePlane: the imaging camera may be a virtual point from which the 3D object is observed, similarly to the above described MPR, information required to establish the camera plane CameraPlane may include following parameters:

(1) Information of a point on the camera plane CameraPlanePos:

The point shall be disposed outside a space corresponding to the 3D image data set VolumeData. Suppose the space of VolumeData has size parameters including Length, Width and Height, then the point on the camera plane may be calculated as follows.

CameraPlanePos=MidPoint−CameraPlaneNormal*(Length+Width+Height)

(2) Normal vector of the camera plane CameraPlaneNormal:

The normal vector of the camera plane extends from the point CameraPlanePos to the point MidPoint of the puncture needle. Suppose the normal vector of the camera plane is parallel with the normal vector of the plane Plane2, then it can be set as follows.

CameraPlaneNormal=Plane2Normal (3) Size of the camera plane:

The size of the camera plane may be set to be the same as the size of the scanned images. Suppose the scanned images have a size 512*512, then the size of the camera plane may be set as follows.

CameraPlaneWidth=512
CameraPlaneHeight=512

(4) Local coordinate vectors of the camera plane:

Referring to FIG. 5, the local coordinate vectors of the camera plane may be set as the same as those of the plane Plane2, which are listed as follows.

CameraPlaneRowVec=Plane2 RowVec
CameraPlaneColVec=Plane2ColVec

After the parameters of the camera plane are obtained, the 3D image may be formed using the volume rendering method. In some embodiments, a ray casting method may be used. Traversal treatments may be implemented to all points on the camera plane, in which rays may be casted from the points along the normal vector of the camera plane. Intersection points of the rays and the VolumeData may be calculated as sample points. These sample points may be processed, and the processed sample points may constitute pixels (Current pixel) of the 3D image. The 3D image may be formed by implementing traversal treatments to each point on the cameraPlane. Processing the sample points may be implemented based on following equation:

$$I(x, r) = \sum_{i=0}^{L/\Delta s} C_\lambda(s_i)\alpha(s_i) \cdot \prod_{j=0}^{i-1}(1 - \alpha(s_j))$$

where $\alpha(s_i)$ stands for the transparency of a pixel corresponding to a sample point, $C\lambda(s_i)$ stands for the color of the sample point, these two values can be pre-set in a program, L stands for the length of the rays, and I(x, r) stands for the pixel value of the processed Current pixel.

Figure 7:
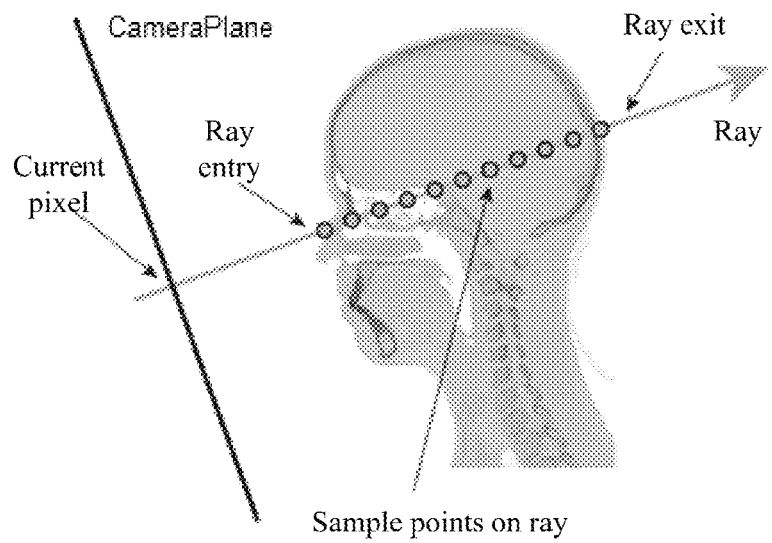
FIG. 7 schematically illustrates a three-dimensional illustration according to one embodiment of the present disclosure.

FIG. 7 schematically illustrates sampling in the 3D image data set VolumeData using ray casting.

Embodiments of image display methods are described above. Variations and modifications can be made based on the above descriptions.

Figure 8:
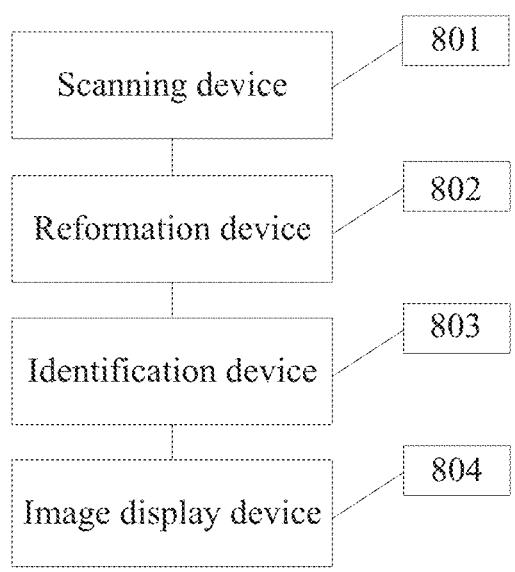
FIG. 8 schematically illustrates a block diagram of a scanning system according to one embodiment of the present disclosure.

FIG. 8 schematically illustrates a block diagram of a scanning system according to one embodiment of the present disclosure.

Referring to FIG. 8, the scanning system may include:

a scanning device 801, adapted to implement a scanning process to obtain scanning data;

a reformation device 802, adapted to convert the scanning data into image data;

an identification device 803, adapted to implement an identification process and a segmentation process to the image data to obtain position and direction information of an interventional device; and a first image display device 804, adapted to calculate a first set of imaging parameters corresponding to a first image display mode based on the obtained position and direction information of the interventional device, and implement real-time image display based on the first set of imaging parameters.

In some embodiments, the scanning device may be a CT system or a MRI system.

In some embodiments, the first image display mode may include at least one selected from multi-planar reformation display, curve-planar reformation display and three-dimensional display.

In some embodiments, when the first image display mode is multi-planar reformation display, the first image display device may include:

a first parameter determination device, adapted to determine imaging parameters for one or more imaging planes based on the obtained position and direction information of the interventional device, where the one or more imaging planes at least include a plane in which the interventional device is disposed, where the imaging parameters for anyone of the one or more imaging planes include coordinate information of a point on the corresponding plane, normal vector of the corresponding plane, size of the corresponding plane and information of local coordinate vectors of the corresponding plane; and a multi-planar reformation device, adapted to establish a three-dimensional image data set based on the image data obtained from the scanning process, obtain one or more multi-planar reformation images based on the three-dimensional image data set and the determined imaging parameters of the one or more imaging planes, and display the multi-planar reformation images.

In some embodiments, the multi-planar reformation device may include:

a plane coordinate calculation unit, adapted to: calculate coordinate information of a left-top point on anyone of the one or more imaging planes based on the coordinate information of the point on the corresponding plane, the normal vector of the corresponding plane, the size of the corresponding plane and the information of local coordinate vectors of the corresponding plane; and implement traversal treatments to points on the one or more imaging planes, so as to obtain coordinate information of the points on the one or more imaging planes based on the coordinate information of the left-top points on the one or more imaging planes, respectively; and an image pixel value obtaining unit, adapted to: obtain image pixel values corresponding to the coordinate information of the points on the one or more imaging planes based on the three-dimensional image data set and the obtained coordinate information of the points on the one or more imaging planes; form the one or more multi-planar images based on the obtained image pixel values; and display the one or more multi-planar images.

In some embodiments, when the one or more imaging planes include more than one plane, the one or more imaging planes include at least a first imaging plane and a second imaging plane, where the first image plane is a plane in which the interventional device is disposed, and the second imaging plane is a plane perpendicular to the first imaging plane. In some embodiments, the first image plane is a plane in which the interventional device is disposed, and the second imaging plane is any plane which is not parallel with the first imaging plane.

In some embodiments, when the first image display mode is curve-planar reformation display, the first image display device may include:

a second parameter determination device, adapted to determine imaging parameters of an imaging curve plane in which the interventional device is disposed based on the obtained position and direction information of the interventional device, where the imaging parameters include information of a curve line along which the interventional device is disposed and size of the curve plane; and a curve plane imaging device, adapted to establish a three-dimensional image data set based on the image data obtained from the scanning process, obtain a curve-planar reformation image based on the three-dimensional image data set and the determined imaging parameters of the curve plane, and display the curve-planar reformation image.

In some embodiments, the scanning method may further include:

a determination device, adapted to determine whether the interventional device has a curve shape based on the obtained position and direction information of the interventional device, if yes, proceed to the curve plane imaging device.

In some embodiments, when the first image display mode is three-dimensional display, the first image display device may include:

a third parameter determination device, adapted to determine parameter information of an imaging camera plane based on the obtained position and direction information of the interventional device; and a three-dimensional imaging device, adapted to establish a three-dimensional image data set based on the image data obtained from the scanning process, obtain a three-dimensional reformation image based on the three-dimensional image data set and the determined parameter information of the imaging camera plane, and display the three-dimensional reformation image.

In some embodiments, the three-dimensional imaging device may include:

a ray casting unit, adapted to implement traversal treatments to points on the imaging camera plane, so as to cast a ray from each point on the imaging camera plane along a normal vector direction of the imaging camera plane; and a processing unit, adapted to calculate intersection points of the rays and the three-dimensional image data set, take the intersection points as sample points, process the sample points using image composition to form the three-dimensional reformation image, and display the three-dimensional reformation image.

It should be noted that, in descriptions of the present disclosure, terms like "first" and "second" are used merely for distinguishing an entity/operation from another entity/operation, which may not require or suggest that the entities/operations must have substantial relationship or order. Moreover, the term "comprising", "including" or any other variants thereof are intended to cover a non-exclusive inclusion, such that a number of processes, methods, articles, or devices including certain elements not only include those elements, but also include other elements not explicitly listed, or include inherent elements for such processes, methods, articles or devices. In the case where no more restrictions are illustrated, elements with limitations of "includes a . . . " do not preclude that there are other same elements included in processes, methods, articles, or devices of the elements.

Embodiments of the present disclosure can be implemented using computer executable instructions executed by a computer, such as program modules. Generally, a program module may include routines, programs, objects, components, data structures, etc., for performing particular tasks or implementing particular abstract data types. Embodiments of the present disclosure also can be implemented in a distributed computing environment, in which tasks are conducted by remote processing devices connected through communication network. In the distributed computing environment, program modules may be disposed in storage mediums, including storage devices, of local and remote computers.

The disclosure is disclosed, but not limited, by preferred embodiments as above. Based on the disclosure of the disclosure, those skilled in the art can make any variation and modification without departing from the scope of the disclosure. Therefore, any simple modification, variation and polishing based on the embodiments described herein is within the scope of the present disclosure.

What is claimed is:

1. An image display method used in a scanning system, the method comprising:
    implementing a scanning process to obtain scanning data;
    converting the scanning data into image data;
    implementing an identification process and a segmentation process to the image data to obtain position and direction information of an interventional device; and
    calculating imaging parameters corresponding to a multi-planar reformation display mode, a curve-planar reformation display mode, or a three-dimensional display mode, and implementing real-time image display based on the imaging parameters,
    wherein if the imaging parameters are calculated corresponding to the multi-planar reformation display mode, the step of calculating the imaging parameters and implementing real-time image display comprises: determining a first set of imaging parameters for one or more imaging planes based on the obtained position and direction information of the interventional device, where the one or more imaging planes at least comprise a plane in which the interventional device is disposed, where the first set of imaging parameters for anyone of the one or more imaging planes comprise coordinate information of a point on the corresponding plane, normal vector of the corresponding plane, size of the corresponding plane and information of local coordinate vectors of the corresponding plane; establishing a three-dimensional image data set based on the image data obtained from the scanning process; obtaining one or more multi-planar reformation images based on the three-dimensional image data set and the determined first set of imaging parameters of the one or more imaging planes; and displaying the one or more multi-planar reformation images, wherein if the imaging parameters are calculated corresponding to the curve-planar reformation display mode, the step of calculating the imaging parameters and implementing real-time image display comprises: determining a second set of imaging parameters of an imaging curve plane in which the interventional device is disposed based on the obtained position and direction information of the interventional device, where the second set of imaging parameters comprise information of a curve line along which the interventional device is disposed and size of the curve plane; establishing a three-dimensional image data set based on the image data obtained from the scanning process; obtaining a curve-planar reformation image based on the three-dimensional image data set and the determined second set of imaging parameters of the curve plane; and displaying the curve-planar reformation image, wherein if the imaging parameters are calculated corresponding to the three-dimensional display mode, the step of calculating the imaging parameters and implementing real-time image display comprises: determining a third set of parameter information of an imaging camera plane based on the obtained position and direction information of the interventional device; establishing a three-dimensional image data set based on the image data obtained from the scanning process; implementing traversal treatments to points on the imaging camera plane, so as to cast a ray from each point on the imaging camera plane along a normal vector direction of the imaging camera plane; calculating intersection points of the rays and the three-dimensional image data set; taking the intersection points as sample points and processing the sample points using image composition to form a three-dimensional reformation image; and displaying the three-dimensional reformation image.

2. The method according to claim 1, wherein the steps of obtaining one or more multi-planar reformation images based on the three-dimensional image data set and the determined first set of imaging parameters of the one or more imaging planes and displaying the multi-planar reformation images comprise:

calculating coordinate information of a left-top point on anyone of the one or more imaging planes based on the coordinate information of the point on the corresponding plane, the normal vector of the corresponding plane, the size of the corresponding plane and the information of local coordinate vectors of the corresponding plane;

implementing traversal treatments to points on the one or more imaging planes, so as to obtain coordinate information of the points on the one or more imaging planes based on the coordinate information of the left-top points on the one or more imaging planes, respectively;

obtaining image pixel values corresponding to the coordinate information of the points on the one or more imaging planes based on the three-dimensional image data set and the obtained coordinate information of the points on the one or more imaging planes;

reconstructing the one or more multi-planar images based on the obtained image pixel values; and displaying the one or more multi-planar images.

3. The method according to claim 1, wherein when the one or more imaging planes comprise more than one plane, the one or more imaging planes comprise at least a first imaging plane and a second imaging plane, where the first image plane is a plane in which the interventional device is disposed, and the second imaging plane is a plane perpendicular to the first imaging plane; or, the first image plane is a plane in which the interventional device is disposed, and the second imaging plane is any plane which is not parallel with the first imaging plane.

4. The method according to claim 1, further comprising:

after the position and direction information of the interventional device is obtained and before the second set of imaging parameters of the imaging curve plane are determined based on the obtained position and direction information of the interventional device, determining whether the interventional device has a curve shape based on the obtained position and direction information of the interventional device, if yes, proceeding to the step of determining imaging parameters of an imaging curve plane in which the interventional device is disposed based on the obtained position and direction information of the interventional device.

5. A scanning system, comprising:

a scanning device, configured to implement a scanning process to obtain scanning data;

a reformation device, configured to convert the scanning data into image data;

an identification device, configured to implement an identification process and a segmentation process to the image data to obtain position and direction information of an interventional device; and a first image display device, configured to calculate imaging parameters corresponding to a multi-planar reformation display mode, a curve-planar reformation display mode, or a three-dimensional display mode, and implement real-time image display based on the imaging parameters, wherein if the first image display device is configured to calculate the imaging parameters corresponding to the multi-planar reformation display mode, the first image display device is further configured to: determine a first set of imaging parameters for one or more imaging planes based on the obtained position and direction information of the interventional device, where the one or more imaging planes at least comprise a plane in which the interventional device is disposed, where the first set of imaging parameters for anyone of the one or more imaging planes comprise coordinate information of a point on the corresponding plane, normal vector of the corresponding plane, size of the corresponding plane and information of local coordinate vectors of the corresponding plane; establish a three-dimensional image data set based on the image data obtained from the scanning process; obtain one or more multi-planar reformation images based on the three-dimensional image data set and the determined first set of imaging parameters of the one or more imaging planes; and display the one or more multi-planar reformation images, wherein if the first image display device is configured to calculate the imaging parameters corresponding to the curve-planar reformation display mode, the first image display device is further configured to: determine a second set of imaging parameters of an imaging curve plane in which the interventional device is disposed based on the obtained position and direction information of the interventional device, where the second set of imaging parameters comprise information of a curve line along which the interventional device is disposed and size of the curve plane; establish a three-dimensional image data set based on the image data obtained from the scanning process; obtain a curve-planar reformation image based on the three-dimensional image data set and the determined second set of imaging parameters of the curve plane; and display the curve-planar reformation image, wherein if the first image display device is configured to calculate the imaging parameters corresponding to the three-dimensional display mode, the first image display device is further configured to: determine a third set of parameter information of an imaging camera plane based on the obtained position and direction information of the interventional device; establish a three-dimensional image data set based on the image data obtained from the scanning process; implement traversal treatments to points on the imaging camera plane, so as to cast a ray from each point on the imaging camera plane along a normal vector direction of the imaging camera plane; calculate intersection points of the rays and the three-dimensional image data set; take the intersection points as sample points and processing the sample points using image composition to form a three-dimensional reformation image; and display the three-dimensional reformation image.

6. The scanning system according to claim 5, wherein the scanning system is a computed tomography system or a magnetic resonance imaging system.

* * * * *